(12) United States Patent
Klein

(10) Patent No.: US 6,572,846 B2
(45) Date of Patent: Jun. 3, 2003

(54) HAIR-TREATMENT COMPOSITIONS

(75) Inventor: Sonja Klein, Hattersheim (DE)

(73) Assignee: Clariant GmbH, Frankfurt (DE)

( * ) Notice: Subject to any disclaimer, the term of this patent is extended or adjusted under 35 U.S.C. 154(b) by 0 days.

(21) Appl. No.: 09/852,933

(22) Filed: May 10, 2001

(65) Prior Publication Data

US 2002/0031487 A1 Mar. 14, 2002

(30) Foreign Application Priority Data

May 12, 2000 (DE) .......................... 100 23 334

(51) Int. Cl.$^7$ .......................... A61K 7/075; A61K 7/06; A61K 6/00
(52) U.S. Cl. .................. 424/70.28; 424/401; 424/70.1; 424/70.15; 424/70.19; 424/70.21; 424/70.27; 514/880
(58) Field of Search .............................. 424/70.1, 70.11, 424/70.21, 70.22, 70.27, 70.28, 70.31, 70.15, 400, 401; 514/880

(56) References Cited

U.S. PATENT DOCUMENTS

| | | | | |
|---|---|---|---|---|
| 4,333,921 A | * | 6/1982 | Luedicke et al. | 424/70 |
| 4,976,956 A | * | 12/1990 | Noe | 424/70 |
| 5,318,727 A | * | 6/1994 | Ohtawa et al. | 252/547 |
| 5,612,025 A | * | 3/1997 | Cauwet-Martin et al. | 424/70.17 |

* cited by examiner

*Primary Examiner*—Michael G. Hartley
*Assistant Examiner*—Sharmila S. Gollamudi
(74) *Attorney, Agent, or Firm*—Richard P. Silverma

(57) ABSTRACT

The invention relates to aqueous hair-treatment compositions comprising one or more quaternary ammonium compounds which are sparingly soluble in water and which contain at least one long-chain alkyl or alkenyl group having at least 18 carbon atoms, one or more water-soluble quaternary ammonium compounds, one or more nonionic, amphoteric and/or zwitterionic solubility promoters and optionally one or more thickeners. The compositions according to the invention are distinguished by a clear and translucent appearance. In particular, the compositions are hair cures and hair rinses.

3 Claims, No Drawings

HAIR-TREATMENT COMPOSITIONS

BACKGROUND OF THE INVENTION

The invention relates to hair-treatment compositions for the care and smoothing of hair. The compositions according to the invention are distinguished by a clear and translucent appearance.

Hair-treatment compositions for the conditioning of human hair have been known for a long time. They generally comprise quaternary ammonium compounds which are sparingly soluble in water and which have at least one long-chain alkyl or alkenyl group. Such compositions are usually formulated as aqueous dispersions or emulsions, microemulsions, gels or else in aerosol form, and are used as hair cures, hair rinses etc.

However, a disadvantage of such compositions is that, due to the sparingly soluble quaternary ammonium compounds, they do not have a clear appearance, but appear dull as a result of their clouding and are not very esthetically pleasing.

SUMMARY OF THE INVENTION

It was therefore an aim to develop aqueous hair-treatment compositions which have a clear and translucent appearance.

DESCRIPTION OF THE PREFERRED EMBODIMENTS

Surprisingly, we have now found that aqueous hair-treatment compositions comprising, as components, A) one or more quaternary ammonium compounds which are sparingly soluble in water and which contain at least one long-chain alkyl or alkenyl group having at least 18 carbon atoms, B) one or more water-soluble quaternary ammonium compounds, C) one or more nonionic, amphoteric and/or zwitterionic solubility promoters and D) optionally one or more thickeners, have a clear and translucent appearance.

The hair-treatment compositions according to the invention preferably comprise, based on the finished hair-treatment composition, 0.1 to 10% by weight, particularly preferably 0.2 to 5% by weight, especially preferably 0.5 to 1.5% by weight, of component A), 0.1 to 20% by weight, particularly preferably 0.5 to 10% by weight, especially preferably 1 to 5% by weight, of component B), 0.1 to 20% by weight, particularly preferably 0.5 to 10% by weight, especially preferably 1 to 5% by weight, of component C) and 0.1 to 15% by weight, particularly preferably 0.3 to 6% by weight, especially preferably 0.5 to 3% by weight, of component D).

Suitable quaternary ammonium compounds A) which are sparingly soluble in water are preferably behenyltrimethylammonium chloride, stearyltrimethylammonium chloride and/or distearyldimethylammonium chloride. Particular preference is given to behenyltrimethylammonium chloride.

Suitable water-soluble quaternary ammonium compounds B) are preferably lauryltrimethylammonium chloride, cetyltrimethylammonium chloride and/or PEG-5 stearylammonium lactate. Particularly preferably suitable are cetyltrimethylammonium chloride and/or PEG-5 stearylammonium lactate.

Suitable as solubility promoters C) are nonionic, amphoteric and/or zwitterionic surfactants.

Suitable as nonionic surfactants are preferably fatty alcohol ethoxylates (alkylpolyethylene glycols); alkylphenol polyethylene glycols; alkyl mercaptan polyethylene glycols; fatty amine ethoxylates (alkylamino polyethylene glycols); fatty acid ethoxylates (acylpolyethylene glycols); polypropylene glycol ethoxylates (Pluronics®); fatty acid alkylolamides (fatty acid amide polyethylene glycols); N-alkyl- and N-alkoxy-polyhydroxy fatty acid amides; sugar esters (e.g. sucrose esters, sorbitol esters) and sugar ethers (e.g. glucose ether); and/or polyglycol ethers.

Suitable amphoteric surfactants are preferably amine oxides, particular preference being given to ($C_{12}$–$C_{18}$)-alkyldimethylamine oxides and fatty acid amidoalkyldimethylamine oxides, very particular preference being given to lauryldimethylamine oxide and cocamine oxide; N-($C_{12}$–$C_{18}$-alkyl)-β-aminopropionates and N-($C_{12}$–$C_{18}$-alkyl)-β-iminodiproprionates in the form of their alkali metal and mono-, di- and trialkylammonium salts; N-acylamidoalkyl-N,N-dimethylacetobetaines, preferably the N-($C_8$–$C_{18}$-acyl)amidopropyl-N,N-dimethylacetobetaines; ($C_{12}$–$C_{18}$)-alkyldimethylsulfopropylbetaines; and/or amphoteric surfactants based on imidazolines (e.g. Miranol® and Steinapon®), preferably the sodium salt of 1-(β-carboxymethyloxyethyl)-1-(carboxymethyl)-2-laurylimidazoline.

Suitable zwitterionic surfactants are preferably alkylamidopropylbetaines, particularly preferably cocamidopropylbetaine; N-alkyl-N,N-dimethylammonium glycinates, e.g. cocoalkyldimethylammonium glycinates; N-acylaminopropyl-N-N-dimethylammonium glycinates; e.g. cocoacylaminopropyldimethylammonium glycinates; 2-alkyl-3-carboxymethyl-3-hydroxyethylimidazolines having in each case 8 to 18 carbon atoms in the alkyl or acyl group; and/or cocoacylaminoethyl hydroxyethylcarboxymethyl glycinate.

Particularly preferred as solubility promoter C) are amine oxides, particularly preferably lauryldimethylamine oxide and/or cocamine oxide.

Suitable thickeners D) are preferably hydroxyethylcellulose; carboxymethylcellulose; polysaccharides, such as, for example, xanthan gum, guar guar, agar agar, alginates, PEG-120 methylglucose dioleate, methylglucose; dioleate; relatively high molecular weight polyethylene glycol mono- and diesters of fatty acids; polyacrylates; polyvinyl alcohols; polyvinylpyrrolidone; surfactants, such as, for example, ethoxylated fatty acid glycerides, esters of fatty acids with polyols (e.g. pentaerythritol), fatty alcohols, fatty alcohol ethoxylates, alkyl oligoglucoside; and/or isopropanolamide mixtures based on coconut fatty acid.

An especially suitable thickener is hydroxyethylcellulose.

The hair-treatment compositions according to the invention may comprise further additives and auxiliaries, such as oily substances, superfatting agents, stabilizers, bodying agents, cationic polymers, silicone compounds, biogenic active ingredients, antidandruff agents, film formers, preservatives, acids, alkalis, buffers, hydrotropic agents, moisture-donating substances, solubilizers, UV absorbers, colorants and/or fragrances.

Suitable oily substances are all known oils, fats and waxes of mineral, animal, vegetable and synthetic origin. Preferred oil and fat components are diallyl ethers having a total of 12–24 carbon atoms, fatty acid esters having a total of 12–26 carbon atoms, liquid hydrocarbons having 10–32 carbon atoms and mixtures thereof. Suitable fatty acid esters are, for example, methyl palmitate, ethyl oleate, isopropyl myristate, n-hexyl laurate, n-butyl stearate, cetyl and stearyl isononanoate. Particular preference is given to paraffin oils, vaseline, vegetable oils, synthetic triglycerides, such as, for example, glyceryl tricaprylate, and silicone oils.

Superfatting agents which may be used are substances such as, for example, lanolin and lecithin, nonethoxylated and polyethoxylated or acylated lanolin and lecithin derivatives, polyol fatty acid esters, mono-, di- and triglycerides and/or fatty acid alkanolamides.

Suitable silicone compounds are, for example, dimethylpolysiloxane, methylphenylpolysiloxanes, cyclic silicones and/or amino-, fatty-acid-, alcohol-, polyether-, epoxy-, fluorine- and/or alkyl-modified silicone compounds, which may either be in liquid form or else in resin form at room temperature.

Suitable biogenic active ingredients are, for example, Bisabolol®, Allantoin®, Phytantriol®, Panthenol®, AHA acids, plant extracts and vitamin complexes.

Antidandruff agents which may be used are Climbazol®, Octopirox®, Oxiconazol® and Zinkpyrethion®.

Customary film formers are chitosan, microcrystalline chitosan, quaternized chitosan, polyvinylpyrrolidone, vinylpyrrolidone/vinyl acetate copolymers, polymers of the acrylic acid series, quaternary cellulose derivatives, collagen, hyaluronic acid and salts thereof and similar compounds.

The acids or alkalis used for adjusting the pH are preferably citric acid and/or sodium hydroxide solution.

To improve the flow behavior, it is possible to use hydrotropic agents, such as, for example, ethanol, isopropyl alcohol, propylene glycol or glucose.

Examples of available moisture-donating substances are isopropyl palmitate, glycerol and/or sorbitol.

Suitable preservatives are, for example, phenoxyethanol, formaldehyde solution, parabens, pentanediol or sorbic acid.

The total amount of auxiliaries and additives in the hair-treatment compositions is preferably 1 to 30% by weight, particularly preferably 2 to 20% by weight.

The hair-treatment compositions according to the invention are preferably hair cures and hair rinses.

The hair-treatment compositions according to the invention are preferably prepared by dissolving components A), B) and C) in water with stirring at temperatures of 45–85° C., preferably 55–75° C., and then cooling the mixture to room temperature and, where appropriate, then adding one or more thickeners D) in the form of an aqueous dispersion or solution to the mixture.

EXAMPLES

The examples below give formulations of inventive hairspray cures (Examples 1 and 2) and hair rinses (Examples 3 to 10). The examples serve to illustrate the invention in more detail but without limiting it. All percentages are percentages by weight.

In addition to the components given in each of the examples, the formulations also comprise citric acid and small amounts of perfume oil, preservative and colorant solution ad 100% by weight of the formulation.

Hairspray cures 1 and 2

To prepare the hairspray cures 1 and 2, a mixture of components I) and II) is prepared in each case. For this, component I) is dissolved in component II) with stirring at about 60° C. until clear. The mixture is then cooled to room temperature. The pH is then adjusted to about pH 4 using citric acid.

| Hairspray cure 1: | | |
|---|---|---|
| I) | Genamin CTAC | 5% |
| | Genamin KDMP | 1% |
| | Genaminox CS | 4% |
| | Cetiol HE | 2% |
| | Panthenol | 0.2% |
| II) | Water | ad 100% |

| Hairspray cure 2: | | |
|---|---|---|
| I) | Genamin KDMP | 1% |
| | Genamin KSL | 5% |
| | Genaminox CS | 4% |
| | Cetiol HE | 2% |
| | Panthenol | 0.2% |
| II) | Water | ad 100% |

Hair rinses 3 to 10

To prepare the hair rinses 3 to 10, a mixture 1 of components I) and II) is prepared in each case. For this, component I) is dissolved in component II) with stirring at about 60° C. until clear. Mixture 1 is then cooled to room temperature. To prepare a mixture 2, component III) is dispersed in component IV) in each case and the mixture is stirred until clear. Mixtures 1 and 2 are then mixed together with stirring. The pH is then adjusted to about pH 4 using citric acid.

| Hair rinse 3: | | |
|---|---|---|
| I) | Genamin CTAC | 5.0% |
| | Genamin KDMP | 1.0% |
| | Genapol DU-080 | 1.0% |
| | Genagen CA-050 | 1.0% |
| II) | Water | 40.0% |
| III) | Tylose H10000 G4 | 2.0% |
| IV) | Water | ad 100% |

| Hair rinse 4: | | |
|---|---|---|
| I) | Genamin CTAC | 5.0% |
| | Genamin KDMP | 0.5% |
| | Genaminox LA | 4.0% |
| | Cetiol HE | 2.0% |
| II) | Water | 37.7% |
| III) | Tylose H 100000YP2 | 0.8% |
| IV) | Water | ad 100% |

| Hair rinse 5: | | |
|---|---|---|
| I) | Genamin CTAC | 5.0% |
| | Genamin KDMP | 0.5% |
| | Genaminox LA | 5.0% |
| | Velsan D8P-3 | 1.0% |
| II) | Water | 27.3% |

Hair rinse 5:

| | | |
|---|---|---|
| III) | Tylose H | 1.2% |
| IV) | Water | ad 100% |

Hair rinse 6:

| | | |
|---|---|---|
| I) | Genamin KSL | 5.0% |
| | Genamin KDMP | 1.0% |
| | Genaminox KC | 6.0% |
| II) | Water | 36.8% |
| III) | Tylose H | 1.2% |
| IV) | Water | ad 100% |

Hair rinse 7:

| | | |
|---|---|---|
| I) | Genamin CTAC | 5.0% |
| | Genamin KDMP | 1.0% |
| | Genaminox CS | 6.0% |
| | Cetiol HE | 2.0% |
| II) | Water | 36.8% |
| III) | Tylose H | 1.2% |
| IV) | Water | ad 100% |

Hair rinse 8:

| | | |
|---|---|---|
| I) | Genamin CTAC | 5.0% |
| | Genamin KSL | 5.0% |
| | Genamin KDMP | 1.0% |
| | Genaminox CS | 6.0% |
| | Cetiol HE | 2.0% |
| | Vitamin E | 0.2% |
| | Vitamin B5 | 0.7% |
| II) | Water | 36.8% |
| III) | Tylose H | 1.5% |
| IV) | Water | ad 100% |

Hair rinse 9:

| | | |
|---|---|---|
| I) | Genamin CTAC | 5.0% |
| | Genamin STAC | 0.5% |
| | Genaminox LA | 4.0% |
| | Cetiol HE | 2.0% |
| II) | Water | 37.7% |
| III) | Tylose H 100000YP2 | 0.8% |
| IV) | Water | ad 100% |

Hair rinse 10:

| | | |
|---|---|---|
| I) | Genamin CTAC | 5.0% |
| | Genamin DSAC | 0.5% |
| | Genaminox LA | 4.0% |
| | Cetiol HE | 2.0% |
| II) | Water | 37.7% |
| III) | Tylose H 100000YP2 | 0.8% |
| IV) | Water | ad 100% |

INCI names of the commercial products used:

| | | |
|---|---|---|
| Genamin KDM-P ® | (Clariant GmbH) | Behenyltrimethyl-ammonium Chloride |
| Genamin KSL ® | (Clariant GmbH) | PEG-5 Stearyl Ammonium Lactate |
| Genamin CTAC ® | (Clariant GmbH) | Cetyltrimethylammonium Chloride |
| Genamin STAC ® | (Clariant GmbH) | Stearyltrimethylammonium Chloride |
| Genamin DSAC ® | (Clariant GmbH) | Distearyl Dimethyl Ammonium Chloride |
| Tylose H 100000 YP2 ® | (Clariant GmbH) | Hydroxyethylcellulose |
| Tylose H | (Clariant GmbH) | Hydroxyethylcellulose |
| Genaminox La | (Clariant GmbH) | Lauryldimethyl Amine Oxide |
| Genaminox KC | (Clariant GmbH) | Cocamine Oxide |
| Genaminox CS | (Clariant GmbH) | Cocamine Oxide |
| Genapol DU-80 | (Clariant GmbH) | Undeceth-8 |
| Velsan D8P-3 | (Clariant GmbH) | Isopropyl PPG-2 Isodeceth-7 Carboxylate |
| Cetiol HE | (Henkel) | PEG-7 Glyceryl Cocoate |
| Genagen CA-050 | (Clariant GmbH) | PEG-5 Cocamide |

What is claimed is:

1. An aqueous hair-treatment composition consisting of:
   A) 0.1 to 10 wt-% of one or more quaternary ammonium compounds selected from the group consisting of behenyltrimethylammonium chloride, stearyltrimethylammonium chloride, distearyldimethylammonium chloride, and mixtures thereof,
   B) 1 to 5 wt-% of one or mare water-soluble quaternary ammonium compounds selected from the group consisting of auryltrimethylammonium chloride, cetyltrimethylamnonium chloride, PEG-5 stearylammonium lactate, and mixtures thereof,
   C) 0.1 to 15 wt-% of one or more amphoteric solubility promoters;
   D) 0.3 to 6 wt-% of one or more thickeners selected from the group consisting of hydroxyethylcellulose carboxymethylcellulose; polysaccharides, relatively high molecular weight polyethylene glycol mono- and diesters of fatty acids; polyacrylates; polyvinyl alcohols; polyvinylpyrrolidone; ethoxylated fatty acid glycerides, esters of fatty acids with polyols, fatty alcohols, fatty alcohol ethoxylates, alkyl oligoglucoside; isopropanolamide mixtures based on coconut fatty acid, and mixtures thereof; and
   E) 1 to 30 wt-% of at least one component selected from the group consisting of stabilizers, preservatives, acids, buffers, UV absorbers, colorants, and fragrances,
   whereby the aqueous hair-treatment has a clear and translucent appearance.

2. A hair spray comprising the hair treatment composition of claim 1.

3. A hair rinse comprising the hair treatment composition of claim 1.

* * * * *